United States Patent
Syvret et al.

(10) Patent No.: US 7,002,040 B2
(45) Date of Patent: Feb. 21, 2006

(54) PROCESS FOR PURIFYING FLUOROXY COMPOUNDS

(75) Inventors: Robert George Syvret, Allentown, PA (US); Philip Bruce Henderson, Allentown, PA (US); Donald Elson Fowler, Coopersburg, PA (US); Beth Ann Campion, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 378 days.

(21) Appl. No.: 10/353,211

(22) Filed: Jan. 28, 2003

(65) Prior Publication Data

US 2004/0146454 A1 Jul. 29, 2004

(51) Int. Cl.
*C07C 53/00* (2006.01)
*C07C 55/00* (2006.01)

(52) U.S. Cl. ............... 562/849; 562/850; 562/853

(58) Field of Classification Search ........ 562/849, 562/850, 853
See application file for complete search history.

(56) References Cited

U.S. PATENT DOCUMENTS

| | | | |
|---|---|---|---|
| 2,689,254 A | 9/1954 | Cady et al. | 260/453 |
| 3,394,163 A | 7/1968 | Kroon | |
| 4,322,394 A | 3/1982 | Mezey et al. | 423/244 |
| 4,499,024 A | 2/1985 | Fifolt | 260/453 |
| 5,523,499 A | 6/1996 | Corbin et al. | |
| 2002/0156321 A1 | 10/2002 | Syvret | |

FOREIGN PATENT DOCUMENTS

JP 2003 226673 A 8/2003

OTHER PUBLICATIONS

Hohorst, et al, *Bis(fluoroxy) difluoromethane*, $CF_2(OF)_2$, JACS, (1967), 89, 1809.
Cauble, et al, *Preparation of Bis(fluoroxy)difluoromethane*, . . . JACS, 89:8, Apr. 12, 1967, 1962.
Lustig, et al, *Preparation of Fluoroxy Compounds*, JACS (1967), 89, 2841.
Kellogg, et al, *Trifluoromethyl Hypofluorite*, JACS (1948), 70, 3986.
Baerlocher, et al, *Atlas of Zeolite Framework Types*, Fifth Ed. 2001, Elsevier, 14-15.
Cauble, et al, *Fluorocarbonyl Hypofluorite*, Dept. Chem. U. of WA, Apr. 26, 1967, 5161-5162.
Wechsberg, et al, *Comparative Studies of the Catalytic . . .*, JACS, 91:16, Jul. 30, 1969, 4432-4436.
Ruff, et al, *A Simple Synthesis of Fluoroxyperfluoroalkyl . . .*, Rohm and Haas Co., Jul. 18, 1966.
Fifolt, et al, *Fluorination of Aromatic Derivatives with . . .*, Am. Chem. Soc., 85 (1950) 4576-4582.
Kennedy, et al, *Reaction of Carbonyl Fluoride With Fluorine . . .*, J. Fluorine Chem., 3 (1973/74) 41-54.

*Primary Examiner*—Sikarl A. WItherspoon
(74) *Attorney, Agent, or Firm*—Geoffrey L. Chase

(57) ABSTRACT

This invention relates generally to a improvement in a process for the purification of fluoroxy compounds, such as bis(fluoroxy)difluoromethane and fluoroxytrifluoromethane produced by the fluorination of carbon oxides. The improvement in effecting purification of the fluoroxy compounds is effected by initially selectively removing the fluorine by contacting with a crystalline zeolite and then removing the carbon oxide by selective adsorption.

15 Claims, No Drawings

PROCESS FOR PURIFYING FLUOROXY COMPOUNDS

BACKGROUND OF THE INVENTION

In early years, bisfluoroxydifluoromethane (BDM) has been used as a reagent for effecting direct fluorination of organic compounds, e.g., effecting the addition of fluorine to the nucleus of an aromatic compound. Fluoroxytrifluoromethane (FTM) or sometimes referred to as trifluoromethylhypofluorite is another fluorinating agent which also has been used as a fluorine source. In recent years, the above two compounds have been used for semiconductor electronics applications such as for etching of dielectric materials, dopants and for chamber cleaning applications.

BDM and FTM are often produced by the CsF-catalyzed reaction of fluorine ($F_2$) and $CO_2$ or CO, as depicted in eq 1 and 2a–b, respectively.

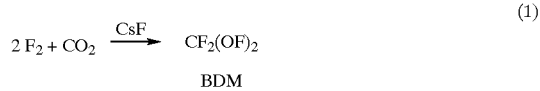
$$2 F_2 + CO_2 \xrightarrow{CsF} CF_2(OF)_2$$
BDM
(1)

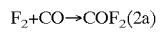
$F_2 + CO \rightarrow COF_2$ (2a)

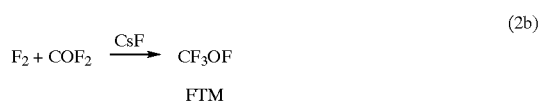
$$F_2 + COF_2 \xrightarrow{CsF} CF_3OF$$
FTM
(2b)

The following patents and articles are illustrative of other processes and variations for producing the fluoroxy compounds.

Hohorst et al, *Bis(fluoroxy)difluoromethane*, $CF_2(OF)_2$, JACS, (1967), 89, 1809, discloses the preparation of BDM in 99.7% yield through the static room temperature reaction between $CO_2$ and a 305% molar excess of $F_2$ in the presence of a large molar excess of CsF.

Cauble et al, *Preparation of Bis(fluoroxy)difluoromethane*, $CF_2(OF)$, JACS, (1967), 89, 1962, discloses the preparation of BDM at room temperature in 99.1% yield by the reaction of fluorocarbonyl hypofluorite with excess $F_2$ in the presence of CsF.

Lustig et al, *Preparation Of Fluoroxy Compounds*, JACS (1967), 89, 2841 disclose a process for the preparation of BDM in 98.0% yield by the reaction of fluorine with carbon dioxide in the presence of cesium fluoride.

Kellogg et al, *Trifluoromethyl Hypofluorite*, JACS (1948), 70, 3986 disclose the synthesis of FTM through the catalytic fluorination of methanol vapor in the presence of a heated catalyst of copper ribbon coated with fluorides of silver. Subsequently, the same type of catalyst was used for the reactions between carbon monoxide (CO) or carbonyl fluoride, $COF_2$, and $F_2$ with the principal product in either case being FTM.

U.S. Pat. No. 4,499,024 discloses the preparation of bisfluoroxydifluoromethane by the continuous reaction of carbon dioxide with fluorine in the presence of cesium fluoride catalyst. The reaction product is trapped in a metal trap, cooled with dry ice and ethanol. The material is distilled and stored in another cylinder.

However, there is a need in the industry for scaleable processes that are capable of generating these kinds of electrophilic fluorination agents (hereinafter referred to as "$F^+$" agents) with sufficient "$F^+$" character, or alternatively, "$F^+$" power, in essentially pure form and in high selectivity. Also, an important criteria is that the processes are safe and allow for economical production of the fluoroxy compounds.

BRIEF SUMMARY OF THE INVENTION

This invention relates generally to a improvement in a process for the purification of a fluoroxy compound, such as BDM, i.e., $CF_2(OF)_2$, and FTM, i.e., $CF_3OF$, produced by the fluorination of carbon oxides. The improvement in effecting purification of the fluoroxy compounds from a gas stream contaminated with unreacted fluorine and carbon oxide is effected by selectively removing the fluorine from the gaseous reaction product by contacting a crystalline zeolite with the gaseous reaction product and sequentially or simultaneously removing the carbon oxide. Preferred zeolites have a pore size sufficiently large to allow fluorine to permeate the pores and react therein but sufficiently small to substantially exclude the fluorine product, e.g., BDM or FTM. In addition the preferred zeolites should be capable of adsorbing the carbon oxides, such as carbon dioxide in the reaction product.

Several advantages in the above process for purifying a reaction mixture obtained from the fluorination of carbon oxides are as follows:

an ability to generate essentially pure fluoroxy compounds, e.g. BDM and FTM;

an ability to eliminate a flow system wherein the fluoroxy compound-containing gas must be collected (trapped at low-temperature) and separated from residual $F_2$; and, an ability to minimize the handling of very dangerous reaction product streams due to (a) the uncertainty of low temperature co-condensing highly energetic and unstable by-products of the fluoroxy compound synthesis reaction, e.g., FC(O)OF and (b) the potential for spark-initiated explosive decomposition of BDM and FTM in the condensed phase.

DETAILED DESCRIPTION OF THE INVENTION

This invention relates to an improvement in a process for the purification of fluoroxy compounds, such as BDM, $CF_2(OF)_2$, and FTM, $CF_3OF$, which are useful as electrophilic fluorination agents, as oxidants, and as etchants. Fluoroxy compounds are prepared by the catalyzed reaction of fluorine with a carbon oxide, e.g., carbon dioxide, carbon monoxide, and COF2. (The term carbon oxide as used herein is intended also to include compounds which may be organic in nature but converted to a carbon oxide in the reaction process, e.g., an alcohol such as methanol.) The reaction product from the manufacturing process is a gaseous mixture comprised of the fluoroxy compound, e.g., BDM or FTM, together with unreacted F2, unreacted carbon oxides, e.g., CO, CO2, and other fluoroxy compounds, e.g., COF2.

As illustrated in the prior art, the common procedure for purifying the gaseous reaction product comprised of the fluoroxy compound has been to pass the gas stream through a cold trap, typically a dry ice and ethanol mixture or liquid nitrogen, fractionally distilling the mixture, and recovering the fluoroxy compound. As stated, the use of a low temperature trap followed by fractional distillation has its disadvantages.

The improvement in the process for the purification of a fluoroxy compound containing gaseous reaction product formed in the fluorination of carbon oxides and comprised of the fluoroxy compound with unreacted F2 and unreacted carbon oxides resides in (a) contacting the gaseous reaction product under conditions for removing the fluorine from the gaseous mixture by selective reaction, and (b) removing the carbon oxides, whereby an essentially pure fluoroxy compound is recovered as product of the process.

Selective reaction of fluorine is achieved by contacting the gaseous reaction product with a crystalline zeolite (molecular sieve) having a pore size sufficiently large to allow the fluorine molecule to permeate the pores thereof and be reacted therein, but sufficiently small to exclude the fluoroxy compound, e.g., BDM or FTM. Selective adsorption of the carbon oxides can also be effected by contacting the gaseous reaction product with a zeolite capable of adsorbing the carbon oxides.

The removal of unreacted fluorine and carbon oxides can be effected substantially simultaneously or sequentially. If a small diameter crystalline zeolite is used, the fluorine may permeate the pores and react therein. If the pore size is too small, it will not allow the carbon oxide to enter and the carbon oxide will pass through with the fluoroxy compound. That effluent may be passed though another crystalline zeolite bed having a pore size sufficient to permit the carbon oxide to enter but insufficient to allow the fluoroxy compound to enter. The pore size of a typical zeolite will range from 3 to 4 Å.

Examples of crystalline zeolites (molecular sieves) include natural and synthetic zeolites. The molecular sieves of this invention are metallosilicates and phosphates stable to dehydration having an effective pore opening of less than 4.6 Å. These are generally referred to as small pore sieves and include the standard 3A and 4A types used in many dehydration operations. They also include other aluminosilicates (i.e. zeolites) known to have a suitable pore size such as chabazite, gismondine, ZK-5 etc. A complete listing of the known 8-ring metallosilicate structures can be found in the "Atlas of Zeolite Framework Types" editors C. Baerlocher, W. M. Meier, and D. Olson, Fifth edition 2001, Elsevier pp 14–15. along with the size of the window openings allowing molecular access to the framework. It should be noted that all eight-ring structures will not be operative for practicing the purification process. It is the combination of framework ring opening and the location of extra framework cations that controls the effective pore size for molecular access. For example both the sodium form in the 4A zeolite and predominantly the potassium form in the 3A Zeolite will effectively exclude the bulk components allowing the fluorine to be sorbed; whereas the Ca form in the 5A zeolite is too large and will not exclude the bulk components. The adsorbents of this invention are not restricted to aluminosilicates but may have other metals in the framework. For example, the aluminophosphate, AlPO-18, has a significant micropore volume only accessible through 3.8A windows.

In a preferred embodiment a crystalline aluminosilicate is selected which is reactive with the fluorine. Although the fluoroxy compound also will be reactive with the crystalline aluminosilicate, the reaction will be limited to the external surface of the crystalline aluminosilicate. The reaction of the fluoroxy compound within the crystalline aluminosilicate is limited by virtue of having selected a crystalline aluminosilicate having a small pore size which precludes permeation by the fluoroxy compound. In a most preferred practice for the selective removal of fluoroxy compound the crystalline aluminosilicate is selected which is substantially simultaneously capable of adsorbing the carbon oxides in addition to effecting reaction with the fluorine. Alternatively, if the fluorine is selectively reacted as for example in a 3A zeolite, the carbon oxides may be adsorbed in a separate step as for example in a 4A zeolite or removed by other means.

Summarizing, crystalline zeolites suited for practicing the purification process for the fluoroxy products, BDM or FTM are the 3A or 4A molecular sieves. When a 3A molecular sieve is used, just $F_2$ is selectively removed and destroyed, i.e., reacted in the purification process. When a 4A molecular sieves is used, $F_2$ is reacted within the pores of the zeolite and the carbon oxides, $CO_2$ or CO and residual $COF_2$ are adsorbed. BDM or FTM pass through the bed of the crystalline zeolite. However, when a large pore zeolite is used, e.g., a 5A and 13X molecular sieve, $F_2$, and the fluoroxy compound, BDM or FTM are both reacted resulting in product yield loss.

Prior to contacting the zeolite with the gaseous reaction mixture containing a fluoroxy compound, the crystalline zeolites must be activated preferably using a thermal activation step. Such a thermal activation step can be achieved by a number of different methods in which the zeolitic water and the hydration spheres associated with the extra-framework cation are carefully removed and the amount of water in the gaseous environment in contact with the zeolite during this step is minimized. That is, the partial pressure of water making such contact should be less than about 0.4 atmospheres, preferably not more than about 0.1 atmospheres at temperatures above about 150° C.

One method of accomplishing activation is to subject the at least binary exchanged X-zeolite composition, which contains up to about 30% by weight of water, to pressures in the range of about 0.1 to 10 atmospheres while maintaining sufficient molar mass velocities and residence times of a flow of a non-reactive purge gas, that is a molar mass velocity of about 0.5 to 100 kilograms mole per meter squared hour and a residence time of no greater than about 2.5 minutes, and then heat the composition at a temperature ramp of 0.1° to 40° C. per minute up to a temperature of at least about 300° C. and no greater than about 650° C. The residence time is defined as the volume of the column or other unit used to thermally activate the zeolite divided by the volumetric flow rate of the purge gas at the standard temperature and pressure. The molar mass velocity is the flow rate of the purge gas divided by the cross-sectional area of the column used for thermal activation. The purpose of the purge gas is to provide a sufficient mass for efficient heat and mass transfer from the surface of the adsorbent at a residence time to limit the water in the purge gas exiting the adsorbent bed to the desired low limits. The minimum residence time is determined by economic and process constraints, although times of less than 0.0025 minutes would appear to provide no advantages.

Another method of thermal activation is to conduct the activation under less than about 0.1 atmospheres vacuum without the use of the purge gas and to heat the material to the desired activation temperature and a ramp temperature of from 0.1° to 40° C. per minute.

Still another method that is available for thermal activation of zeolitic adsorbents is the use of microwave radiation, conditions that are described in U.S. Pat. No. 4,322,394, of which the description of the microwave procedure for thermally activating zeolites is incorporated herein by reference.

In summary, the crystalline aluminosilicate is selected preferably such that it is reactive with the unreacted fluorine and adsorptive toward the carbon oxides, $CO_2$ or CO and $COF_2$. In that way, the fluorine is removed and the carbon oxides are adsorbed leaving only a pure fluoroxy compound product, e.g., BDM or FTM in the product stream. Some large pore reactive adsorbents, e.g., allow too much of the fluoroxy compound into the pore structure. Reaction occurs between the fluoroxy compound and the crystalline zeolite. As a result, one obtains reduced yields of product. When activated carbon is used for BDM purification, $F_2$, and the fluorinated compound, BDM, are absorbed and/or reacted and therefor the fluorine and fluorinated compound are not separated.

The purification process can be operated at any achievable temperature, preferably from −78 to 50° C., and most preferably at ambient temperature, and at ambient pressure.

This improved purification method offers the advantages of being scaleable to commercial volumes, practical to implement, cost effective (since materials are commercially and readily available), and safe to practice since the purification can be done at ambient temperature and there is no requirement to dangerously condense these product gases.

The following examples are intended to illustrate various embodiments of the invention and are not intended to restrict the scope thereof.

EXAMPLE 1

Production of BDM and Low Pressure Manufacture and Purification Using 4A Molecular Sieves A mixture of 17% $CO_2$/17% $F_2$/balance $N_2$ was passed at a total flow of 60 standard cubic centimeters (sccm) over a pelletized $CeF_4$/CsF catalyst bed at 30 psig bed pressure. The residual $F_2$ in the gaseous reaction product was measured as 1.2% by ultraviolet spectroscopy (UV). The gas-phase infrared (IR) spectrum of the product gas mixture showed only BDM and $CO_2$.

The gaseous reaction product gas was flowed to a column filled with an activated 4A molecular sieve, i.e., crystalline aluminosilicate (4A molecular sieves are activated by thermal activation using flowing nitrogen). The $F_2$ concentration of the gas mixture exiting the bed immediately dropped from 1.7% to 0.7% (near the lower detectable limit) and the BDM IR spectrum disappeared. After 5 minutes of continuous flow, the BDM spectrum reappeared in the IR spectrum. (Presumably, the BDM and $F_2$ reacted initially with the outside surface of the 4A molecular sieve.) Once the outside surface had been fully reacted (passivated), then only the $F_2$ was destroyed inside the pores. The BDM apparently is excluded from the pores of the 4A molecular sieve. Also, the analysis showed that the $CO_2$ spectrum disappeared after the product gas mixture was passed through the bed. $CO_2$ is physically adsorbed by the 4A crystalline aluminosilicate. In addition, no $SiF_4$ or other volatile fluorides were observed in the BDM product gas mixture purified by 4A molecular sieves. The reaction is terminated when the fluorine or carbon oxide concentration in the gas stream exiting the column begins to increase.

To increase product yield, it may be preferred to pass a fluorine containing gas stream through the crystalline aluminosilicate prior to passing the gaseous reaction product through the column and thereby prereact the surface sites of the molecular sieve. In that way the fluoroxy compound as product will not be consumed by the surface sites.

EXAMPLE 2

Production of BDM and Low Pressure Manufacture and Purification Using 3A Molecular Sieves A mixture of 50% $CO_2$/10% $F_2$/balance $N_2$ was passed at a total flow of 100 sccm over a pelletized $CeF_4$/CsF bed at 30 psig. The residual $F_2$ in the product gas was measured as 0.8% by ultraviolet spectroscopy (UV). The gaseous reaction product infrared (IR) spectrum showed only BDM and $CO_2$.

The gaseous reaction product gas was flowed to a column filled with activated 3A molecular sieve (3A molecular sieves are activated by drying using known methods). The $F_2$ concentration of the product gas mixture exiting the bed immediately dropped and the BDM IR spectrum disappeared. After several minutes of continuous flow, the BDM spectrum reappeared in the IR spectrum and the $F_2$ concentration reading stabilized at 0.5%, which is the approximate lower detectable limit due to the interference from BDM. In this example, the $CO_2$ is not adsorbed; however, the $F_2$ still has access to the internal pore structure and is destroyed. In addition, no $SiF_4$ or other volatile fluorides are observed in the BDM product gas mixture purified by 3A molecular sieves.

EXAMPLE 3

Purification of BDM Using 3A Molecular Sieves (High Flow/High Pressure Manufacture and Purification)

A mixture of 200 sccm $CO_2$ and 200 sccm 10% $F_2$/balance $N_2$ was passed through a powdered CsF bed at 100 psig bed pressure. The residual $F_2$ in the product gas was measured as 0.6% by ultraviolet spectroscopy (UV). The gas-phase infrared (IR) spectrum of the product gas mixture showed only BDM and $CO_2$.

The product gas mixture was flowed to a column filled with activated 3A molecular sieve (3A molecular sieves are activated by drying using known methods). The $F_2$ concentration of the product gas mixture exiting the bed immediately dropped and the BDM IR spectrum disappeared. After a short period of continuous flow, the BDM spectrum reappeared in the IR spectrum and the $F_2$ concentration reading stabilized at 0.3%. In addition, no $SiF_4$ or other volatile fluorides are observed in the BDM product gas mixture purified by 3A molecular sieves.

EXAMPLE 4

Production of BDM

High Flow/Moderate Pressure Manufacture and Purification Using 3A Molecular Sieves A mixture of 145 sccm $CO_2$ and 200 sccm 10% $F_2$/balance $N_2$ was passed through a powdered CsF bed at 50 psig bed pressure. The residual $F_2$ in the product gas was measured as 1.2% by ultraviolet spectroscopy (UV). The gaseous reaction product infrared (IR) spectrum of the product gas mixture showed only BDM and $CO_2$.

The product gas mixture was flowed to a column filled with activated 3A molecular sieve (3A molecular sieves are activated by drying using known methods). The $F_2$ concentration of the product gas mixture exiting the bed immediately dropped and the BDM IR spectrum disappeared. After a short period of continuous flow, the BDM spectrum reappeared in the IR spectrum and the $F_2$ concentration reading stabilized at 0.5%. In addition, no $SiF_4$ or other volatile fluorides are observed in the BDM product gas mixture purified by 3A molecular sieves.

EXAMPLE 5

Production of FTM

High Flow/Moderate Pressure Manufacture and Purification Using 3A Molecular Sieves A mixture of approximately 12 sccm CO and 200 sccm 10% $F_2$/balance $N_2$ was passed through a bed of CsF catalyst (supported on zirconia) at a constant bed pressure of 100 psig. The residual $F_2$ in the gaseous reaction product was measured as 4.6% by ultraviolet spectroscopy (UV). The gas-phase infrared (IR) spectrum of the product gas mixture showed only FTM.

The gaseous reaction product was then flowed to a column filled with activated 3A molecular sieve (3A molecular sieves are activated by drying using known methods). The $F_2$ concentration of the product gas mixture exiting the bed immediately dropped, while the IR spectrum of the product gas indicated that the FTM product remained. After a short period of continuous flow, the $F_2$ concentration reading stabilized at 0.4%. In addition, no $SiF_4$ or other volatile fluorides, including the intermediate $COF_2$, are observed in the FTM product gas mixture purified by 3A molecular sieves. Apparently, the molecular sieve bed absorbed/reacted with most of the residual $F_2$ while having little or no affect on the FTM product.

COMPARATIVE EXAMPLE A

Attempted Purification of BDM Using 5A Molecular Sieves

In an experiment similar to those described in Examples 1 and 2, a product gas mixture containing BDM and residual $CO_2$ and $F_2$ was passed through a column of activated 5A molecular sieves, i.e., crystalline aluminosilicates. Unlike the procedure of Examples 1 and 2, the gas exiting the molecular sieve bed did not contain BDM, $CO_2$, or $F_2$. Presumably, in this example, $CO_2$ was absorbed by the molecular sieve bed and the BDM and $F_2$ were reacted out. Presumably the pores were now big enough to allow BDM to enter and react with the molecular sieve material.

COMPARATIVE EXAMPLE B

Attempted Purification of BDM Using Coconut Charcoal

In an experiment similar to that described in Comparative Example A, a gaseous reaction product containing BDM and residual $CO_2$ and $F_2$ was passed through a column of activated coconut charcoal. The gas exiting the charcoal bed contained only $CO_2$ and did not contain BDM or $F_2$. Presumably, in this example, $CO_2$ is not absorbed by the charcoal whereas BDM and $F_2$ are either reacted out, or perhaps adsorbed.

COMPARATIVE EXAMPLE C

Attempted Purification of BDM Using 5A Molecular Sieves

In an experiment similar to that described in Comparative Example A, a gaseous reaction product containing BDM and residual $CO_2$ and $F_2$ was passed through a column of activated 5A molecular sieves. Unlike Example 1 and 2 the gas exiting the 5A molecular sieve bed did not contain BDM, $CO_2$, or $F_2$. In addition, the temperature of the 5A molecular sieve bed increased dramatically. Presumably, in this example, all species were absorbed by the molecular sieve bed and the BDM and $F_2$ are reacted out causing the temperature to increase.

COMPARATIVE EXAMPLE D

Attempted Purification of BDM Using 13X Molecular Sieves

In an experiment similar to that described in Comparative Example C, a gaseous reaction product containing BDM and residual $CO_2$ and $F_2$ was passed through a column of activated 13X molecular sieves. The gas exiting the 13X molecular sieve bed did not contain BDM, $CO_2$, or $F_2$. In addition, the temperature of the 13X molecular sieve bed increased dramatically, even more so than that observed in Example C. Presumably, in the present example, all species are again absorbed by the molecular sieve bed and the BDM and $F_2$ were reacted out causing the temperature to increase dramatically.

COMPARATIVE EXAMPLE E

Attempted Purification of FTM Using 13X Molecular Sieves

In an experiment similar to that described in Example 5, a gaseous reaction product containing FTM, residual $COF_2$, and $F_2$ was passed through a column of activated 13X molecular sieves. The gas exiting the molecular sieve bed did not contain FTM, $COF_2$, or $F_2$. In addition, the temperature of the 13X molecular sieve bed increased very dramatically. Presumably, in this example, all species are absorbed/reacted by the molecular sieve bed causing the temperature to increase very dramatically.

COMPARATIVE EXAMPLE F

Attempted Purification of FTM Using 5A Molecular Sieves

In an experiment similar to that described in Example 5 and Comparative Example E, a gaseous reaction product containing FTM, residual $COF_2$, and $F_2$ was passed through a column of activated 5A molecular sieves. The gas exiting the molecular sieve bed did not contain FTM, $COF_2$, or $F_2$. In addition, the temperature of the 5A molecular sieve bed increased very dramatically. Presumably, in this example, all species are absorbed/reacted by the molecular sieve bed causing the temperature to increase very dramatically.

What is claimed is:

1. In a process for the purification of a fluoroxy compound present in a gaseous reaction product produced by the fluorination of carbon oxide, said gaseous reaction product containing fluorine, fluoroxy compound, and carbon oxide, the improvement for effecting purification of said fluoroxy compound which comprises:

(a) contacting the gaseous reaction product with a crystalline zeolite under conditions for selectively removing the fluorine from the gaseous reaction product, and (b) removing the carbon oxide, whereby an essentially pure fluoroxy compound is recovered as a product of the process.

2. The process of claim 1 wherein the pore size of the crystalline zeolite is sufficiently large to allow fluorine and carbon oxide to permeate the pores and react or be absorbed therein but sufficiently small to substantially exclude the fluoroxy compound.

3. The process of claim 2 wherein the crystalline zeolite has an effective pore size less than 4.6 Å.

4. The process of claim 2 wherein the crystalline zeolite is a 4 A zeolite.

5. The process of claim 1 wherein the fluorine is removed by effecting contact of the gaseous reaction product with a 3A crystalline aluminosilicate thereby generating an effluent essentially free of fluorine and then removing the carbon oxide by effecting contact of the effluent with a 4A crystalline aluminosilicate.

6. In a process for the purification of a bis(fluoroxy)difluoromethane present in a gaseous reaction product produced by the fluorination of carbon oxide, said gaseous reaction product containing fluorine, bis(fluoroxy)difluoromethane, and carbon oxide the improvement for effecting purification of said bis(fluoroxy)difluoromethane which comprises:

(a) contacting the gaseous reaction product under conditions with a crystalline zeolite for selectively removing the fluorine from the gaseous reaction product, and (b) removing the carbon oxides, whereby an essentially pure bis(fluoroxy)difluoromethane compound is recovered as a product of the process.

7. The process of claim 6 wherein the crystalline zeolite is a crystalline aluminosilicate.

8. The process of claim 7 wherein the crystalline aluminosilicate has an effective pore size less than 4.6 Å.

9. The process of claim 8 wherein the crystalline aluminosilicate is a 3A molecular sieve.

10. The process of claim 8 wherein the crystalline aluminosilicate is a 4A molecular sieve.

11. In a process for the purification of fluoroxytrifluoromethane present in a gaseous reaction product produced by the fluorination of a carbon oxide, said gaseous reaction product containing fluorine, fluoroxytrifluoromethane, and carbon oxide the improvement for effecting purification of said fluoroxytrifluoromethane which comprises:

(a) contacting the gaseous reaction product with a crystalline zeolite under conditions for selectively removing the fluorine from the gaseous reaction product, and (b) removing the carbon oxides, whereby an essentially pure fluoroxytrifluoromethane compound is recovered as a product of the process.

12. The process of claim 11 wherein the crystalline zeolite is a crystalline aluminosilicate.

13. The process of claim 12 wherein the crystalline aluminosilicate has an effective pore size less than 4.6 Å.

14. The process of claim 13 wherein the crystalline aluminosilicate is a 3A molecular sieve.

15. The process of claim 13 wherein the crystalline aluminosilicate is a 4A zeolite.

* * * * *